United States Patent
Hansson (10) Patent No.: US 9,737,631 B2
(45) Date of Patent: Aug. 22, 2017

(54) SILICONE FILM

(71) Applicant: Mölnlycke Health Care AB, Göteborg (SE)

(72) Inventor: Dennis Hansson, Gunnilse (SE)

(73) Assignee: MÖLNLYCKE HEALTH CARE AB, Göteborg (SE)

( * ) Notice: Subject to any disclaimer, the term of this patent is extended or adjusted under 35 U.S.C. 154(b) by 0 days.

(21) Appl. No.: 14/653,621

(22) PCT Filed: Dec. 19, 2013

(86) PCT No.: PCT/EP2013/077518
§ 371 (c)(1),
(2) Date: Jun. 18, 2015

(87) PCT Pub. No.: WO2014/096273
PCT Pub. Date: Jun. 26, 2014

(65) Prior Publication Data
US 2015/0335780 A1   Nov. 26, 2015

(30) Foreign Application Priority Data
Dec. 21, 2012  (EP) .................................... 12199049

(51) Int. Cl.
*A61L 24/04* (2006.01)
*A61L 15/58* (2006.01)
*C09J 183/06* (2006.01)

(52) U.S. Cl.
CPC .............. *A61L 24/046* (2013.01); *A61L 15/58* (2013.01); *C09J 183/06* (2013.01); *C09J 2483/003* (2013.01)

(58) Field of Classification Search
CPC ........ A61L 24/046; A61L 15/58; C09J 183/06
See application file for complete search history.

(56) References Cited

U.S. PATENT DOCUMENTS

| | | |
|---|---|---|
| 5,103,812 A | 4/1992 | Salamone et al. |
| 5,948,400 A | 9/1999 | Brett |
| 6,627,216 B2 | 9/2003 | Brandt et al. |

(Continued)

FOREIGN PATENT DOCUMENTS

WO   WO-2009/031948 A1   3/2009

OTHER PUBLICATIONS

International Search Report mailed by the International Searching Authority on Jan. 27, 2014 for International Application No. PCT/EP2013/077518, which was published as WO/2014/096273 on Jun. 26, 2014 (Inventor—Hansson; Applicant—Mölnlycke Health Care AB) (4 pages).

*Primary Examiner* — Daniel Lee
(74) *Attorney, Agent, or Firm* — Ballard Spahr LLP (57) ABSTRACT

Disclosed herein is a method of attaching a medical device to a surface, the medical device having at least one adhesive area, wherein the method comprises the steps of: contacting the surface with a composition comprising a T silicone resin and/or a DT silicone resin and/or an MQ silicone resin and/or an MT silicone resin, thereby providing non-tacky coating on the surface; and attaching the adhesive area to the surface such that the composition is located between, and in contact with, the surface and the adhesive area, thereby attaching medical device to the surface; thereby achieving an improve adherence between the medical device and the surface.

14 Claims, 2 Drawing Sheets

(56) References Cited

U.S. PATENT DOCUMENTS

| | | |
|---|---|---|
| 6,958,154 B2 | 10/2005 | Andolino Brandt et al. |
| 8,263,720 B1 | 9/2012 | Salamone et al. |
| 8,852,648 B2 | 10/2014 | Salamone et al. |
| 8,877,882 B1 | 11/2014 | Salamone et al. |
| 2007/0202245 A1 | 8/2007 | Gantner et al. |
| 2008/0114278 A1* | 5/2008 | Fabo ............... A61F 13/023 602/48 |
| 2012/0095109 A1 | 4/2012 | Garaud et al. |
| 2014/0220843 A1* | 8/2014 | Liu ................. A61L 15/585 442/149 |
| 2014/0287642 A1* | 9/2014 | Kumar .............. C09J 7/025 442/290 |

* cited by examiner

SILICONE FILM

CROSS-REFERENCE TO RELATED APPLICATIONS

The present application is a U.S. National Phase Application of International Application No. PCT/EP2013/077518, filed Dec. 19, 2013, which claims priority to European Patent Application No. 12199049.3, filed Dec. 21, 2012, each of which are hereby incorporated by reference in their entirety.

FIELD OF INVENTION

The present invention relates to a method for attachment of a medical device to a surface.

BACKGROUND OF THE INVENTION

One of the most important functions of the human skin is to provide a barrier of the body towards the environment. A wound caused by an injury or disease may be treated by the use of a bandage or wound dressing to promote healing by preventing infection and leakage from the wound. Dressings used for wounds are often provided with a self-adhering adhesive, also known as pressure-sensitive adhesive (PSA), which purpose is to adhere to the skin surrounding the wound and to fixate the dressing in a desirable position. Various adhesives are available for affixing medical products on the skin, some of the most common being encompassed by the terms acrylic adhesives, and hot melt adhesives, among others.

In order to ensure that a medical device such as a wound dressing remains in the same position after a certain time of use an adhesive having a strong adherence, e.g. an acrylic adhesive, may be used. However, in case that the medical device is to be attached directly on the skin, an acrylic based adhesive increases the risk for pain and damages to the skin when such medical device is to be removed from the skin, e.g. due to skin stripping.

There are a number of commercially available skin products "film forming barrier" products or "skin sealant" products that address the problem of skin stripping by providing a protective layer on the skin before applying a pressure-sensitive adhesive thereto. Such products typically contain a protective polymer dissolved into fast-drying carrier solvent which upon application to the skin evaporates off to leave a film of the protective polymer on the skin. Examples of such products include: Cavilon™ No Sting Barrier Film (3M) containing acrylic terpolymer in hexamethyldisiloxane, Skin Prep™ (Smith & Nephew) containing a butyl ester of polyvinyl/maleic anhydride copolymer in isopropyl alcohol, Shield Skin™ (Mentor) containing a modified polyester and acrylic resin in isopropyl alcohol; and Bard® Protective Barrier Film (Bard Medical) and AllKare™ Protective Barrier Wipe (Convatec) both containing n-butyl and iso-butyl methacrylate in isopropyl alcohol.

U.S. Pat. No. 5,948,400 discloses a method of applying a pressure-sensitive adhesive wound dressing and a water-based skin treatment composition including a water dispersible film-forming polyester resin, a polyol plasticizer, and water, wherein a coating of the liquid composition is applied to the skin adjacent a wound and allowed to form a dry film prior to applying a pressure sensitive dressing over the wound. The dried film bonds strongly to the pressure sensitive adhesive of the dressing but is relatively easily removed from the skin and thus serves to reduce the force needed to remove the dressing, i.e. the coating according U.S. Pat. No. 5,948,400 reduces the total adherence between the dressing and the skin.

U.S. Pat. No. 8,263,720 B1 discloses crosslinked siloxy-containing polymers and their inclusion in liquid adhesive materials that can be used as sacrificial coatings under more adherent materials for protecting skin and mucous membranes. The sacrificial coating is weakly adhesive and may therefore be removed without damaging the skin when the more adherent material is removed. Thus, the coating of U.S. Pat. No. 8,263,720 B1 also reduces the total adherence between the more adherent material and the skin. The polymers of U.S. Pat. No. 8,263,720 B1 are all acrylate- or vinyl-based polymers, i.e. consisting of an acrylate- or vinyl-based backbone, having siloxy-containing pendant groups to increase solubility in hexamethyldisiloxane and/or to crosslink said acrylate- or vinyl-based polymers, and the coating of U.S. Pat. No. 8,263,720 B1 may therefore be regarded as a skin sealant of the same kind as the previously mentioned Cavilon™ No Sting Barrier Film (3M).

Soft silicone gel adhesives are known in the art (see e.g. WO2009031948) to be very gentle on the skin, in contrast to harder adhesives e.g. acrylic adhesives. This is because a soft adhesive can follow the contours of the skin well thus giving a large contact surface area. Thus, although the actual adhesive force in each contact point of a silicone gel adhesive is less than that of an acrylic adhesive, the large surface area of contact achieved with a silicone gel affords a high overall adherence to the skin, whilst at the same time being skin-friendly, i.e. when a silicone gel adhesive is removed from the skin very few skin cells are removed due to the low adhesive force in each contact point, thus the above mentioned problem of skin stripping can be avoided.

Although a soft silicone gel adhesive generally has good adhesion to a skin surface, for some applications, for example when used in a dressing to be applied on areas which are difficult to dress due to the 3D shape thereof and/or areas which are affected by body movements e.g. sacrum, elbow and knee, there may be a need for a stronger adhesion to the skin.

Furthermore, a soft silicone gel adhesive does typically not adhere equally well to a polymeric surface such as a polyurethane film which may be a problem in case a medical devices is to be attached to an area including two different surfaces. For example, in case a second medical device is to be attached to a wound area where a first medical device is already attached, the adhesive area of the second medical device to be applied on top of the first medical device would cover both a skin surface e.g. around the first medical device and a polymeric surface e.g. backing layer of the first medical device.

In general the adhesiveness of a dressing may be improved by increasing the amount of adhesive. However, an increased amount of adhesive leads to an increased manufacturing cost as well as less comfort due to lower breathability and increased thickness of the dressing. Further, the total adherence between medical device including a pressure-sensitive adhesive and a surface may be improved by first applying a layer of an adhesive coating on the surface prior to application of the pressure-sensitive adhesive thereto, for example, a coating of a BIO-PSA® containing a silicone adhesive may be provided on the surface. However, due to the high tack of such coating there is a risk of undesirable adhesion of objects and the handling of such coating is therefore in general troublesome.

Hence, there is a need in the art to further improve the overall adherence of a medical device to the skin or to other medical devices, while avoiding the drawbacks outline above.

SUMMARY OF THE INVENTION

In view of the above-mentioned and other drawbacks of the prior art, a general object of the present invention is to provide a method of attaching a medical device to a surface, in particular a method wherein an improved adherence between a medical device and a surface is achieved.

According to a first aspect of the invention, these and other objects are achieved through a method of attaching a medical device to a surface, the medical device having at least one adhesive area, wherein the method comprises the steps of: contacting the surface with a composition comprising a T silicone resin and/or a DT silicone resin and/or an MQ silicone resin and/or an MT silicone resin, thereby providing a non-tacky coating on the surface; and attaching the adhesive area to the surface such that the composition is located between, and in contact with, the surface and the adhesive area, thereby attaching medical device to the surface.

The invention is based on the realization that an improved adherence between an adhesive area of a medical device and a surface can be achieved by first providing a non-tacky coating of a composition comprising a T silicone resin and/or a DT silicone resin and/or an MQ silicone resin and/or an MT silicone resin on the surface before attaching the adhesive area thereto.

Silicone resins such as MQ resins are known in the art for its use as additives in adhesives in order to increase the stickiness/tackiness thereof. Silicone resins are also used as additives in various skin products such as sunscreen products, hand lotions, make-up, skin care and cosmetics, wherein the silicone resins function to improve the adhesive properties, water resistance and stability of the products. However, in the research work leading to the present invention, it was surprisingly found that T silicone resin and/or a DT silicone resin and/or an MQ silicone resin and/or an MT silicone resin are useful to achieve a non-tacky coating giving improved adherence between an adhesive area of a medical device and a surface.

By an "improved adherence" is meant that the adherence of the adhesive area of the medical device to the surface is stronger if a non-tacky coating is provided, as compared to the adherence of the adhesive area of the medical device to the surface if no non-tacky coating is provided. The stronger total adherence is due to: 1) a higher adherence of the adhesive area of the medical device to the non-tacky coating, as compared to the adherence of the adhesive area of the medical device to the surface directly, as well as 2) a higher adherence of the non-tacky coating to the surface, as compared to the adherence of the adhesive area of the medical device to the surface.

Typically, a substantial part of the non-tacky coating of the present invention will remain on the surface when the medical device is removed. The adhesive failure will mainly occur at the interface between the non-tacky coating and the adhesive area of the medical device. Thereby, the non-tacky coating may be re-used, as a fresh medical device may be adhered to the non-tacky coating remaining on the surface.

By the term "non-tacky coating" should, in the context of this application, be understood as a coating which in its dried state has a surface tack less than 1 N, for example less than 0.1 N, such as less than 0.05N as measured by the FINAT Test Method 9 Loop tack measurement on a coating having a coating weight of 5 $g/m^2$, further described below.

The non-tacky feature of the coating according to the invention facilitates the handling of the surface provided with the non-tacky coating, and so undesirable adhesion of objects e.g. clothing and particles to the coating can be avoided. Accordingly, the improved adherence between the coating and a medical device as achieved through the inventive method is not due to any adhesiveness of the coating but rather due to the chemistry and surface properties of the composition.

In embodiments of the invention, the at least one adhesive area may advantageously comprise a soft silicone gel adhesive. The inventors have surprisingly found that an adhesive comprising soft silicone gel exhibits excellent adherence to a surface having a coating of a composition comprising a T silicone resin and/or a DT silicone resin and/or an MQ silicone resin and/or an MT silicone resin.

The term "silicone gel" refers to a silicone gel that comprises a cross-linked network including silicone of lower molecular weight. The term "soft silicone gel" is intended to encompass silicone gels having a softness (penetration) of from 8 to 22 mm, for example 12 to 17 mm, as measured by a method based on ASTM D 937 and DIN 51580, further discussed below.

By the term "coating" it should be understood at least one continuous layer or a plurality of dots.

In embodiments of the invention, the surface may be a dermal surface.

In embodiments of the invention, the surface may be a polymeric surface, such as, for example, a polyurethane film, which film may be part of a medical device, e.g. the film may be a backing film of a medical device.

The term "surface" should be understood as at least one surface e.g. dermal surface or polymeric surface, however, in embodiments of the invention, the step of contacting the surface with the composition may involve applying a non-tacky coating on several surfaces, for example both a skin surface and a polymeric surface. For example, in case a second medical device is to be attached on a skin surface where a first medical device is already present, the coating may be applied on top of both the first medical device and the surrounding skin surface prior to application of the second medical device thereon.

The term "resin" should, in the context of this application, be understood as three-dimensionally crosslinked polysiloxanes having a backbone of silicon and oxygen atoms. Commercial silicone resins known in the art include "MT silicone resin" "MQ silicone resins", "T silicone resins" and "DT silicone resins".

The term "MQ silicone resin", as used herein, are macromolecular polymers comprised primarily of M-units having the general formula $R_3SiO_{1/2}$, and Q-units having the general formula $SiO_{4/2}$, wherein R is a hydroxyl group, a monovalent and/or a functionally substituted C1-C6 hydrocarbon group, for example a methyl group, methoxy or ethoxy group, or a phenyl group, typically a methyl group, and wherein the ratio of the number of M-units and number of Q-units is 0.5-2, such as for example 0.5-1.5 or 0.5-1.0, such as 0.65-0.70.

The term "MT silicone resin", as used herein, are macromolecular polymers comprised primarily of M-units having the general formula $R_3SiO_{1/2}$, and T-units having the general formula $RSiO_{3/2}$, wherein R is a hydroxyl group, a monovalent and/or a functionally substituted C1-C6 hydrocarbon group, for example a methyl group, methoxy or ethoxy group, or a phenyl group, typically a methyl group, and wherein the ratio of the number of M-units and number of T-units is 0.4-1.8, such as for example 0.4-1.3 or 0.4-0.9, such as 0.5-0.7.

The term "DT silicone resin", as used herein, are macromolecular polymers comprised primarily of D-units having the general formula $R_2SiO_{2/2}$, and T-units having the general formula $RSiO_{3/2}$, wherein R is a hydroxyl, a monovalent or functionally substituted C1-C6 hydrocarbon group, for example a methyl group, methoxy or ethoxy group, or a phenyl group, typically a methyl group, and wherein the ratio of the number of R-groups and number of Si atoms is $1.0<R:Si \leq 1.7$, for example $1.0<R:Si \leq 1.4$.

The term "T silicone resin", as used herein, are macromolecular polymers comprised primarily of T-units having the general formula $RSiO_{3/2}$, wherein R is a hydroxyl, a monovalent or functionally substituted C1-C6 hydrocarbon group, for example a methyl group, methoxy or ethoxy group, or a phenyl group, typically a methyl group.

As would be understood by the skilled person in the art, the "MQ silicone resin", as defined above, may also include a limited amount of D-units and/or T-units, however, by the term "MQ silicone resin" it should be understood a resin wherein at least 80 mol % of the resin molecules are comprised of M-units and Q-units. The "MT silicone resin", as defined above, may include a limited amount of D-units and/or Q-units, however, by the term "MT silicone resin" it should be understood a resin wherein at least 80 mol % of the resin molecules are comprised of M-units and T-units. Further, the "T silicone resin", as defined above, may include a limited amount of D-units and/or M-units and/or Q-units, however, by the term "T silicone resin" it should be understood a resin wherein at least 80 mol % of the resin molecules are comprised of T-units. Similarly, the "DT silicone resin", as defined above, may include a limited amount of M-units and/or Q-units, however, by the term "DT silicone resin" it should be understood a resin wherein at least 80 mol % of the resin molecules are comprised of D-units and T-units.

Furthermore, the "MQ silicone resin", "MT silicone resin", "T silicone resin" and "DT silicone resin" as defined above are typically a solid, having an average molecular weight from 1,000 to 20,000 g/mol, for example from 1,000 to 10,000 g/mol.

For example, the composition may comprise at least one silicone resin of the commercially available resins: SilForm flexible resin, Wacker-Belsil® PMS MK and Wacker-Belsil® TMS 803.

In embodiments of the invention, the composition may further comprise a solvent selected from the group consisting of hexamethyldisiloxane (HMDS), dimethicone, cyclopentasiloxane, C9-C13 isoparafin, isopropyl myristate, ethyl acetate, ethanol, and isopropanol, such as, for example, hexamethyldisiloxane (HMDS).

It is advantageous to provide the composition in the form of a liquid solution, i.e. including a solvent, since this allows for a favorable distribution of the composition upon application. For example, when the surface on which the composition is applied is a dermal surface, the provision of the composition in liquid form renders it possible to cover all contours and wrinkles of the dermal surface. A continuous coating that conforms to the contours of the dermal surface is thereby achieved, resulting in a high total contact area between the coating and the dermal surface. This in turn results in a high adherence between the coating and the dermal surface. In addition, the coating having such high total contact area also provides a sealing effect, that is, the coating prevents e.g. micro-organisms, such as bacteria, to enter in between the coating and the dermal surface.

For example, in embodiments of the invention, the composition may comprise a mixture of: from 1 to 50 weight percent of the T silicone resin and/or the DT silicone resin and/or the MQ silicone resin and/or the MT silicone resin; and from 50 to 99 weight percent of the solvent, such as from 1 to 25 weight percent of the T silicone resin and/or the DT silicone resin and/or the MQ silicone resin and/or the MT silicone resin; and from 75 to 99 weight percent of the solvent. For example, the composition may comprise a mixture of: from 1 to 10 weight percent of the T silicone resin and/or the DT silicone resin and/or the MQ silicone resin and/or the MT silicone resin; and from 90 to 99 weight percent of the solvent, such as 2 weight percent of the T silicone resin and/or the DT silicone resin and/or the MQ silicone resin and/or the MT silicone resin; and 98 weight percent of the solvent.

In order to achieve the above discussed improved adherence between an adhesive area of a medical device and a surface, the composition may advantageously comprise a mixture of: at least 1 weight percent of the T silicone resin and/or the DT silicone resin and/or the MQ silicone resin and/or the MT silicone resin, and 99 weight percent or less of the solvent. However, in case a barrier effect is also desirable, i.e. if the coating, in addition to its function as an adhesion promoter, should function as a protection layer on the surface (e.g. to protect a dermal surface against micro-organisms and peri-wound skin maceration), the composition may advantageously comprise a mixture of at least 10 weight percent of the T silicone resin and/or the DT silicone resin and/or the MQ silicone resin and/or the MT silicone resin, and 90 weight percent or less of the solvent.

In embodiments of the invention, the composition may advantageously comprise a mixture of: from 1 to 25 weight percent of the T silicone resin, and/or the DT silicone resin and/or the MQ silicone resin and/or the MT silicone resin; and from 75 to 99 weight percent of the solvent. Thereby, the viscosity of the composition may be adapted such that the composition can be well distributed over the surface and well follow the contours thereof, thus achieving a large contact area between the composition and the surface.

In embodiments of the invention, the step of step of contacting the surface may involve applying the composition in the form of a spray, mousse, aerosol, foam, or by brush, or by stick, or by roller, or by spreading with a spatula, or by a sponge applicator, or by release by a release sheet.

In embodiments of the invention, the method may further comprise a step of drying the composition on the surface, prior to the step of attaching the adhesive area to the surface. For example, the step of drying may involve evaporating the solvent, after which step a non-tacky coating of the composition is achieved.

In other embodiments of the invention, the composition may not include a solvent, in which case the composition may be applied as a powder on the surface to thereby achieve a non-tacky coating of the composition on the surface.

In embodiments of the invention, the medical device may for example be a wound dressing, a film dressing, a film dressing included as part of a negative pressure wound treatment (NPWT) device, a fixation device, a scare treatment dressing, a drug delivery patch or an ostomy device.

In embodiments of the invention the step of contacting the surface may involve providing a continuous coating or film of the composition on the surface, wherein the coating having a thickness/coating weight (dry weight) in the range from 0.01 to 30 g/m², for example from 0.01 to 20 g/m² such as from 0.01 to 10 g/m², for example from 0.05 to 5 g/m², or from 0.1 to 1 g/m², such as 0.13 g/m².

According to a second aspect of the invention, these and other objects are achieved by the use of a composition comprising a T silicone resin and/or DT silicone resin and/or an MQ silicone resin and/or an MT silicone resin for increasing the adherence between a medical device and a surface, wherein the composition, in use, is located between, and in contact with, the medical device and the surface.

According to third aspect of the invention, these and other objects are achieved through a kit for attachment of a medical device to a surface, the medical device having at least one adhesive area, wherein the kit comprises: means for contacting the surface with a composition comprising a T silicone resin and/or DT silicone resin and/or an MQ silicone resin and/or an MT silicone resin; and a label indicating that adhesive area is to be attached to the surface such that the composition is located between, and in contact with, the surface and the adhesive surface, thereby attaching the medical device to the surface.

In embodiments of the invention the means for contacting the surface may, for example, be a container comprising the composition, which container may for example be a spray flask, or the container may include a sponge applicator, a brush, a stick or a roller to facilitate the application of the composition.

In embodiments of the invention the kit may further comprise a medical device having at least one adhesive area. For example, the adhesive area may comprise a coating of a soft silicone gel adhesive.

BRIEF DESCRIPTION OF THE DRAWINGS

These and other aspects of the invention will now be showed in more detail, with reference to the appended drawings showing an exemplary embodiment of the invention, wherein.

DESCRIPTION OF EXAMPLE EMBODIMENTS OF THE INVENTION

In the following description, the present invention is described with reference to a method for attachment of a medical device to a surface, wherein the medical device comprises at least one adhesive area which is attached to the surface by first providing a non-tacky coating of a composition comprising a T silicone resin and/or a DT silicone resin and/or an MQ silicone resin and/or an MT silicone resin before attaching the at least one adhesive area thereto, thereby enhancing total adherence between the medical device and the surface.

Figure 1:
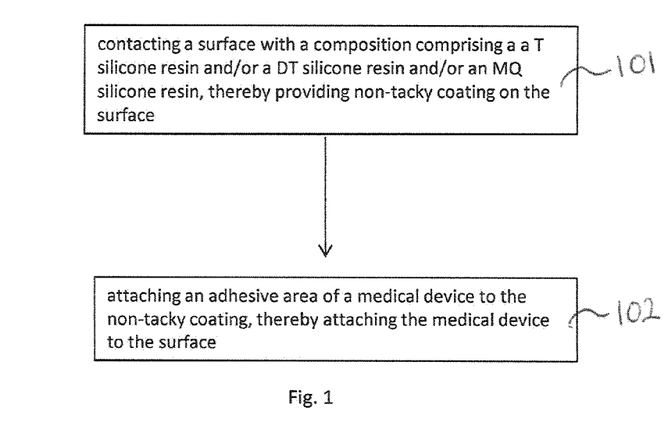
FIG. 1 is a flow chart schematically illustrating a method of attaching a medical device to a surface.

An embodiment of a method of attaching a medical device to a surface according to the invention will now be described with reference to FIG. 1 which is a flow chart schematically illustrating such a method and FIGS. 2a-b (cross-sectional views) and FIGS. 2c-e (top views) which schematically illustrate the surface to which a medical device is attached according to the method of FIG. 1 in states following the corresponding method steps.

Figure 2A:
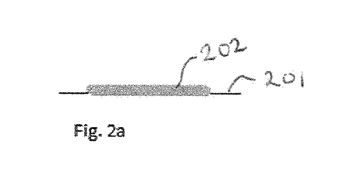
FIGS. 2a-f schematically illustrate the surface to which a medical device is attached according to the method of FIG. 1 in states following the corresponding method steps.
Figure 2B:
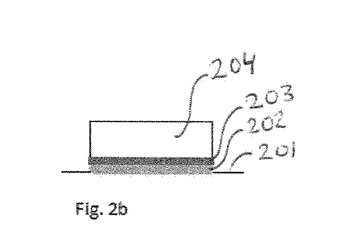

The first step 101 involves contacting a surface 201 with a composition comprising a T silicone resin and/or a DT silicone resin and/or an MQ silicone resin and/or an MT silicone resin, thereby providing non-tacky coating 202 on the surface 201 as shown in FIG. 2a.

In embodiments of the invention, the composition may be in the form of a solid, e.g. a powder, thereby achieving the non-tacky coating directly after applying the composition. Alternatively, as discussed further below, the composition may include a solvent, thus the composition may be a liquid mixture, e.g. a solution or suspension, in which case the method may typically comprise a further step of drying, e.g. evaporating, the solvent after which step the non-tacky coating is formed.

The non-tacky characteristic of the coating achieved through the invention facilitates the handling of a surface having such coating, as no object or article will automatically stick to the coating unless the article includes some adhesive means. It should thus be understood that the non-tacky coating does not provide or function as an adhesive area by itself, but rather the non-tacky coating functions as a non-tacky adhesion promoter to which an adhesive, for example a soft silicone gel adhesive, may advantageously be attached.

For example, in embodiments of the invention, the surface of the coating may have a surface tack of less than 1 N, for example less than 0.1 N, such as less than 0.05N as measured by the FINAT Test Method 9 Loop tack measurement on a coating having a coating weight of 5 g/m², further described below.

The surface may typically be a dermal surface, but may also be other surfaces on, for example, a first medical device to which surface a second medical device is to be attached, including for example any surfaces of a polymeric material such as polyurethane film or foam. For example, in case a second wound dressing including a soft silicone gel adhesive is to be applied onto a wound area where there is already a first wound dressing present, at least part of the silicone gel adhesive of the second wound dressing may overlap a surface of the first wound dressing which surface may be a polymeric film e.g. polyurethane film. As soft silicone gel adhesive does typically not adhere as well to polyurethane films as it does to a skin surface, the inventive method may advantageously be used to improve the adherence i.e. by contacting the polyurethane film (and possibly also the proximal skin surface) with the composition according to the invention before attaching the second wound dressing thereto.

The composition may further comprise a solvent selected from the group consisting of hexamethyldisiloxane (HMDS), dimethicone, cyclopentasiloxane, C9-C13 isoparafin, isopropyl myristate, ethyl acetate, ethanol, isopropanol. For example, the solvent may advantageously comprise hexamethyldisiloxane (HMDS) as T, DT, MQ, and MT silicone resins are highly soluble in HMDS. Further advantages with HMDS include: high volatility which allows for a quick drying and coating/film-forming step (e.g. for a coating weight of ca. 0.1 g/m² such step is typically completed within 20 seconds at room temperature and atmospheric pressure), it does not cause a cooling effect upon evaporation from the skin, and that it is not soluble in blood. In case the composition comprises a solvent, the composition may typically comprise a mixture of: from 1 to 50 weight percent of the T silicone resin and/or the DT silicone resin and/or the MQ silicone resin and/or an MT silicone resin; and from 50 to 99 weight percent of the solvent. For example, the composition may comprise a mixture of: from 1 to 25 weight percent of the T silicone resin and/or the DT silicone resin and/or the MQ silicone resin and/or the MT silicone resin; and from 75 to 99 weight percent of the solvent. For example, the composition may comprise a mixture of: from 1 to 10 weight percent of the T silicone resin and/or the DT silicone resin and/or the MQ silicone resin and/or the MT silicone resin; and from 90 to 99 weight percent of the solvent, such as 2 weight percent of the T silicone resin and/or the DT silicone resin and/or the MQ silicone resin and/or the MT silicone resin; and 98 weight percent of the solvent.

Thereby, the composition may be a liquid mixture which may be applied by means of, for example, a sponge applicator, a brush, or a stick, or a roller, or by spreading with a spatula, or by release by a release sheet, or the liquid mixture may be in the form of a spray, mousse, aerosol, or foam which may be directly applied to the surface.

In case the composition includes a solvent, the composition may advantageously have a relatively low viscosity during application thereof, in order to allow it to penetrate the surface structure and/or sufficiently wet the surface. For example, the viscosity of the composition may be within the range of 0.65 to 500 mPas.

For example, in case of a dermal surface, having a composition in the form of a liquid mixture may be particularly advantageous as the solid particles of the T silicone resins and/or the DT silicone resins and/or the MQ silicone resins and/or the MT silicone resin of the composition may be evenly distributed over the skin surface and in all contours and wrinkles thereof to thereby afford a high contact surface and thus adherence between the coating and the skin.

Typically, the thickness of the coating/or coating weight after drying may be in the range of from 0.01 to 30 $g/m^2$, for example from 0.01 to 20 $g/m^2$, such as from 0.01 to 10 $g/m^2$, for example from 0.05 to 5 $g/m^2$, or from 0.1 to 1 $g/m^2$, such as 0.1 $g/m^2$.

Figure 2C:
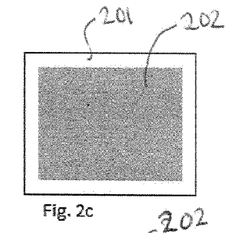
Figure 2D:
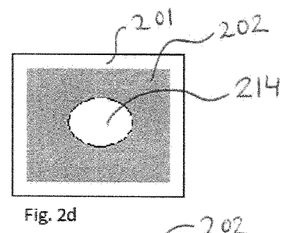
Figure 2E:
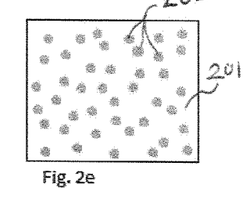
Figure 2F:
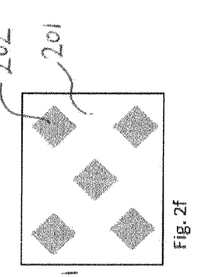

The shape or form of the coating is typically adapted on the surface to fit with a given application or use, as exemplified in FIGS. 2c-f. Typically, the size of the area of the coating is adapted to fit with a given size of the adhesive area of the medical device to be attached thereto. FIG. 2c shows one continuous non-tacky coating 202 (or layer) of the composition on the surface 201, whereas in FIG. 2d the coating 202 is provided on a skin surface 201 around an opening 214 in the skin, which opening 214 may for example be a wound, or the opening 214 may be there because of an object projecting out from the body, in which case that the medical device to be applied may be an ostomy device. For example, the medical device may be an NPWT device in which case a wound cavity, e.g. opening 214 (if present) may be first filled with a wound filler, e.g. a foam or gauze, and subsequently the opening is sealed by attaching a film dressing to the coating 202 on skin surface 201 around the opening 214. FIG. 2e shows the coating 202 in the form of spots (or circular areas) on a surface 201, and FIG. 2f shows the coating 202 in the form of a plurality of square areas on a surface 201.

In the next step 102, illustrated in FIG. 2b, an adhesive area 203 of a medical device 204 is attached to the surface 201 such that the coating 202 comprising the composition is located between, and in contact with, the surface 201 and the adhesive area 203, thereby achieving a strong adhesion between the medical device 204 and the surface 201.

The adhesive area of the medical device may advantageously comprise a silicone gel adhesive, for example a soft silicone gel adhesive. The present inventors have surprisingly found that such soft silicone gel exhibits excellent adherence to a composition comprising a T silicone resin and/or a DT silicone resin and/or an MQ silicone resin and/or an MT silicone resin. For example, the soft silicone gel adhesive may have a softness of 8 to 22 mm, such as 12 to 17 mm, as measured by a method based on ASTM D 937 and DIN 51580, further discussed below. For example, suitable soft silicone gel adhesives can be composed of an addition-cured RTV (Room Temperature Vulcanizing) silicone system which, after admixture, crosslinks and forms a self-adhesive elastomer. Examples of a commercially available RTV addition-cured silicone systems is Wacker SilGel 612 which is a two-component system, wherein the softness and degree of adherence of the formed elastomer can be varied by varying the proportions of the two components A:B from 1.0:0.7 to 1.0:1.3. Other examples of soft silicone adhesives are NuSil MED-6340, NuSil MED3-6300 and NuSil MED 12-6300 from NuSil Technology, Carpmrjeria, Ga., USA, and Dow Corning 7-9800 from Dow Corning Corporation, Midland, USA.

Accordingly, by first providing a coating on a surface prior to attaching the adhesive area of a medical device thereto, an improved adherence between the medical device and the surface is achieved, as compared with the attachment of the same medical device directly on the surface. This is because according to the invention, the bond strength between the non-tacky coating and the adhesive area, and the bond strength between the non-tacky coating and the surface, are both stronger than the bond strength between the adhesive area and the surface (without coating), thus the coating according to the invention increases the total adherence between the dressing and the surface.

Further, in addition to achieving an improved adherence as discussed above, the composition according to the invention may also function as a protective layer on the skin, e.g. to protect the skin from micro-organisms, or to avoid (peri-wound) skin maceration.

The composition according to embodiments of the invention may, for example, comprise at least one (commercially available) silicone resin selected from the group consisting of SilForm Flexible Resin, Wacker-Belsil® PMS MK and Wacker-Belsil® TMS 803. As discussed above, there are a number of commercially available "film forming barrier" products or "skin sealant" products which provides a polymeric coating on the skin after evaporation of the solvent, for example, Cavilon™ No Sting Barrier Film (3M) containing acrylates terpolymer in hexamethyldisiloxane, and Skin Prep™ (Smith & Nephew) containing a butyl ester of polyvinyl/maleic anhydride copolymer in isopropyl alcohol. However, as shown by comparative examples, discussed further below (see Table 1 and Table 2), these products provide no or little enhanced adherence effect in case that the adhesive area comprises a soft silicone gel adhesive. This is because none of these products contain the composition as defined by claim 1. The Cavilon™ product showed no improved adherence when provided between a polyurethane film surface and an adhesive area including a soft silicone gel adhesive, as compared to 108% increased adherence when a coating of Wacker-Belsil® PMS MK (composition according to the invention) was tested. The Skin Prep™ product showed an increase in adhesion of 6% when provided between a skin surface and an adhesive area including a soft silicone gel adhesive, as compared to a 22% increase in adhesion for a coating of Wacker-Belsil® TMS 803 (composition according to the invention) in the same test.

In embodiments of the invention, the medical device may be a wound or film dressing, for example, any one of the following commercially available wound dressings may advantageously be used in the method according to the invention: Mepilex®, Mepilex® lite, Mepilex® Border, Mepilex® Border lite, Mepiform®, Mepitac®, Mefilm®, Mepitel® One and Avance® Film.

Additionally, variations to the disclosed embodiments can be understood and effected by the skilled person in practicing the claimed invention, from a study of the drawings, the disclosure, and the appended claims. For example, in addition to T silicone resins and/or DT silicone resins and/or MQ silicone resins and/or MT silicone resins, the composition may comprise a silicone polymer or silicone co-polymer, for example, polydimethyl siloxane (PDMS), polymethyl phenyl siloxane, polydiphenyl siloxane, polyhedral oligosilsesquioxan (POSS), modified POSS, polyalkyl methyl siloxane polyacrylate siloxane, polyether siloxane or polyester siloxane, polyurethane siloxane, polyurea siloxane and combinations of these or corresponding polymers. Examples of silicone polymers and silicone co-polymers are Dow Corning Corporation, Midland, USA: FA 4001 CM (silicone acrylate) or Dow Corning® 1501 Fluid (polydimethyl siloxane); and Wacker Chemie AG: Belsil® P101 (silicone acrylate), Wacker Geniomer® (polyurethane siloxane), Wacker® AK and the like, or combinations thereof. The composition can also comprise one or more of the following additives: fillers, such as clay, talc, ZnO; and/or skin care agents such as Aloe vera, silicone oil etc.

Other silicone resins and silicone polymers and silicone co polymers can also be used as well as other solvents that are useful in dissolving silicone. Further, as indicated above, a number of means to apply the coating can be used such as, for example, spraying, painting, rolling on, spreading with spatula, foam, textile or nonwoven etc. For example, the composition can be filled into a pen, and be applied to the desired surface by use of the pen, or the composition may be applied through a sponge applicator, a brush, a stick or a roller, alternatively, the composition can be initially coated on a release sheet, and subsequently transferred to the skin by pressing the coated release sheet against the desired surface. The methods listed above are only examples of suitable application methods, the scope of the present invention is not limited by means of applying the composition.

The advantages of the invention have been demonstrated in experiments.

EXAMPLES

Method for Measuring the Softness/Penetration of Soft Silicone Gel Adhesive

Figure 3A:
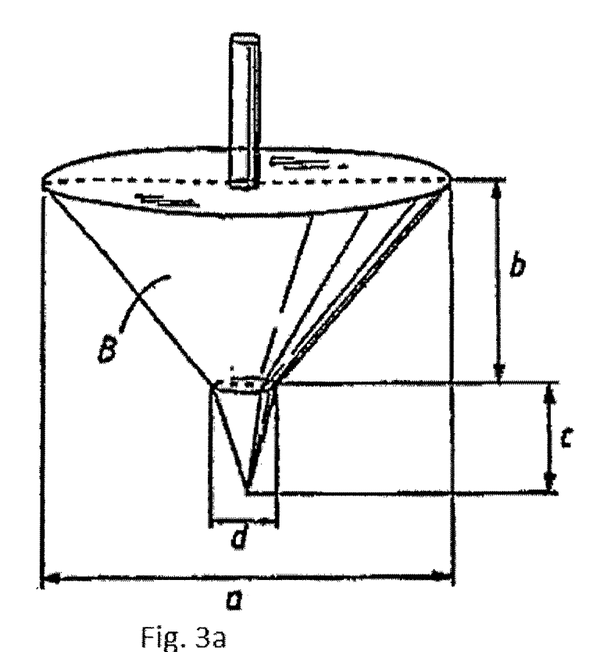
FIGS. 3a-b are schematic illustrations of a method for measuring softness of silicone gel adhesive.
Figure 3B:
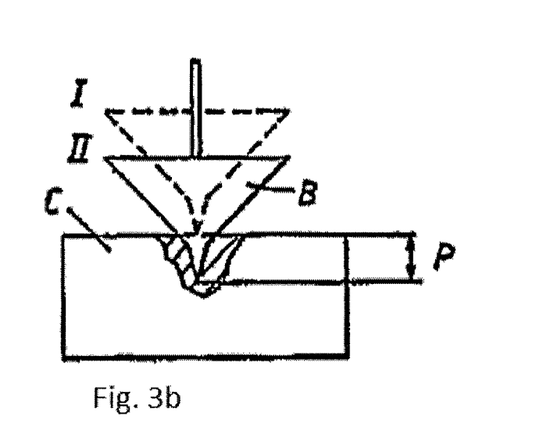

The method used for measuring the softness/penetration of soft silicone gel adhesive is based on ASTM D 937 and DIN 51580, however deviates in a few steps which are explained below. FIGS. 3a-b illustrate this modified method for measuring softness in an adhesive by letting a cone B having a weight of 62.5 g penetrate a test specimen C by gravity, said specimen being made of the adhesive, the softness of which is to be determined, and having a thickness of 30 mm. The test specimen is obtained by filling a cylindrical container having an inner diameter of 60 mm and an inner height of 35-40 mm, with adhesive up to a height of 30 mm. When testing a silicone gel, uncured silicone pre polymer is filled into the container, and this pre polymer will then crosslink into a gel in the container. The cone used is shown in FIG. 3 and has the following measurements a=65 mm, b=30 mm, c=15 mm and d=8.5 mm. The method for determining softness includes lowering of the cone B to a position, indicated with dashed lines, in which the tip of the cone just touches the surface of the test specimen C. The cone B is then released so that it is allowed to penetrate the test specimen C due to gravity. The extent of penetration, i.e. the distance by which the cone has penetrated the test specimen in mm is measured after 5 seconds, and represents the penetration value P, which is larger, the softer the test specimen is. A penetrometer PNR 10 from Sommer & Runge K G, Germany, is used in the method.

Adhesion Test on a Polyurethane Surface

The adhesion effect of various composition was evaluated according to the standard method ASTM D 3330M-02, method F, by measuring the adhesive force between a polyurethane surface coated with a layer of the respective compositions and the adhesive area of Mepiform® (a Mölnlycke Health Care AB dressing including a soft silicone gel adhesive) attached to said coated surface.

Comparative tests were performed with the following compositions:

Cavilon® (registered by 3M), which is a co-polymer including three different monomers: phenyl silicone and an acrylate terpolymer. As discussed above, Cavilon® is a commercial product used for skin protection.

Wacker-Belsil® PMS MK (composition according to the invention), which essentially is a T silicone resin consisting of monomers of the following structure: —$(CH_3SiO_{3/2})$— having the INCI name polymethylsilsesquioxane (PMS). Wacker-Belsil® PMS MK is a solid (typically a powder), solvent free silicone resin.

Wacker-Belsil® TMS 803 (composition according to the invention), which is an MQ silicone resin consisting of a co-hydrolysis product of tetraalkoxysilane (Q unit) and trimethylethoxysilane (M unit), having the INCI name trimethylsiloxysilicate. The chemical structure of Wacker-Belsil® TMS 803 can be seen as a three-dimensional network of polysilicic acid units, which are endblocked with trimethylsilyl groups. The resin may contain some residual ethoxy and hydroxy functions. The average molecular weight can be adjusted precisely via the ratio of M to Q units, which ratio is 0.66 for Wacker-Belsil® TMS 803. Wacker-Belsil® TMS 803 is a solid (typically a powder), solvent free silicone resin.

1:1 mixture of Wacker-Belsil® TMS 803 and Wacker-Belsil® PMS MK (compositions according to the invention);

FA 4001 CM from Dow Corning, which is a co-polymer of acrylate and silicone used as binder in cosmetics;

Wacker Silgel® 612 30:100 A:B, which is soft silicone gel adhesive commercially available from Wacker, which silicone gel is of similar type as the one used as soft silicone gel in wound dressing products, such as Mepiform®. Silgel® 612 is a two component (A and B, above) room temperature vulcanized (2 RTV) silicone with platinum catalyst.

All samples were prepared in a concentration of 2% by weight in hexamethyldisiloxane (HMDS). The sample was applied to one side of a strip of a polyurethane by spraying, giving an approximate coating weight of 0.13 $g/m^2$ after evaporation of HMDS (by drying at room temperature). The coated strip was fixated to a stainless steel plate with a double sided adhesive tape, and the adhesive area of Mepiform® was attached to the coated area on the strip. Subsequently, the Mepiform® was drawn off from the strip at an angle of 90°. The average required removal force, i.e. adhesive force, was measured. The test procedure was repeated for each test strip/sample. Comparative tests with no coating were also performed. The average value and the standard deviation were determined based on 10 measurements for each sample.

The materials were conditioned at 23±2° C. and 50±2% relative atmospheric humidity under at least 4 hours for the substrates with compositions and 4 hours for the Mepiform® product.

As shown in Table 1 below, the T silicone resin (Wacker-Belsil® PMS MK) affords a significant improvement (108%) of the adherence between the film dressing (Mepiform®) and the PU film, also the MQ silicone resin (Wacker-Belsil® TMS 803) and the 1:1 mixture of T (Wacker-Belsil® PMS MK) and MQ (Wacker-Belsil® TMS 803) silicone resins improve the same adherence significantly (by 66% and 91%, respectively), as compared with adhesive force measured between the reference PU film (no coating) and the film dressing (Mepiform®). In contrast, pre-coating with Cavilion®, Dow Corning® FA 4001 CM, and Wacker Silgel® 612 30:100 A:B give no improvement on or an actual decrease in the same measured adherence. Accordingly, these experiments clearly illustrate the claimed technical effects of the invention.

TABLE 1

| Composition in HMDS wt-% | Adhesion between treated PU film and Mepiform ® (N) |
| --- | --- |
| Reference without coating | 0.95 |
| Cavilon ® from 3M | 0.96 |
| 2% Wacker-Belsil ® PMS MK | 1.98 |
| 2% Wacker-Belsil ® TMS 803 | 1.58 |
| 1% Belsil ® PMS MK, 1% Belsil ® TMS 803 | 1.81 |
| 2% Dow Corning ® FA 4001 CM | 0.93 |
| 2% Wacker Silgel ® 612 30:100 A:B | 0.5 |

A Study to Assess the Peel Force of an Adhesive Dressing with and without Skin Surface Pre Treatment in Normal Volunteer Subjects This study was designed to determine the adhesion of a dressing product that uses Safetac® adhesive technology (as in Mepilex® Border), i.e. a dressing having an adhesive area comprising a soft silicone gel adhesive, with and without skin surface pre treatment. The study was a within subject comparison of the adhesion of a Mepilex® Border dressing to skin pre treated with two products (Wacker-Belsil® TMS 803, 2% in HMDS and SkinPrep™) compared to adhesion to untreated skin. The test site was the lower back. Three test sites were identified on the lower back corresponding to the three test conditions; Wacker-Belsil® TMS 803 pre-treatment, SkinPrep™ pre-treatment and no pre-treatment. The dressings in 12.5 cm×2.5 cm strips were applied in duplicate in the same manner vertically to the lower back in a parallel array using an even pressure 1 to 2 minutes after skin pre treatment. The dressings were then removed after a further 60 minutes using a specially designed device and the peel force of dressing removal was recorded. The device measured the force required to peel the test strips off of the skin surface at an angle of 135° to the skin surface at a constant speed of 25 mm per second. The test was carried out in a room with the temperature maintained between 21 and 23° C.

The results of the study show that the force required to remove varied according to skin surface pre-treatment. The results are summarized in Table 2 below:

TABLE 2

| Peel Force | No pre treatment | Wacker-Belsil ® TMS 803 pre treatment | SkinPrep ™ pre Treatment |
| --- | --- | --- | --- |
| Mean | 2.057 | 2.507 | 2.187 |
| SD | 0.471 | 0.530 | 0.482 |
| Median | 1.944 | 2.400 | 2.090 |

The mean value for sites pre-treated with Wacker-Belsil® TMS 803 were higher than for sites pre-treated with SkinPrep™ and higher than sites with no pre-treatment. The mean values for Wacker-Belsil® TMS 803 were approximately 22% higher than no pre-treatment indicating greater adhesion to the skin surface. In contrast pre-treatment with SkinPrep™ only resulted in an increase of approximately 6%.

Statistical analysis using a multiple comparison procedure (Tukey-HSD) indicated that the adhesion at sites pre-treated with Wacker-Belsil® TMS 803 was significantly higher than for sites pre-treated with SkinPrep™ ($p=0.0001$) and sites with no pre-treatment ($p<0.0001$). In addition there was no significant difference in adhesion at sites pre-treated with SkinPrep™ and sites with no pre-treatment.

In conclusion the results of this study show that pre treatment of the skin surface with Wacker-Belsil® TMS 803 led to an increase in adhesion of Safetac®. This conclusion is based on an increased peel force of removal of Safetac® at one hour after application. This increase was approximately 22% based on the mean values compared to untreated skin sites and was statistically significant ($p<0.0001$). In contrast the application of SkinPrep™ led to a smaller increase of approximately 6% based on the mean values compared to untreated skin sites. The difference between adhesion at sites pre-treated with SkinPrep™ and sites with no pre-treatment was not statistically significant ($p=0.4106$).

Method of Measuring the Tack of the Surface of the Coating

The surface tack was measured by the FINAT Test Method 9 (version 2009) Loop tack measurement. OH film X-475 from Folex Imaging, Art.no 3475.0.440, was used as the substrate on which the compositions were coated. The different compositions were made into 15% by weight in HMDS, giving an average measured coating weight of ca. 5 g/m$^2$ after drying of the solvent (HMDS), and draw downs was made with a 50 μm SIMEX coater. The solvent was dried of by first putting the films on a heated plate at 100° C. for 2 minutes and thereafter the coated films were stored for 24 hours before loop tack measurement.

The measured adhesive (maximum) force (N), i.e. the surface tack, for each composition tested is presented in Table 3 below. As shown in Table 3, all tested compositions within the claimed invention, e.g. Wacker-Belsil® PMS MK, Wacker-Belsil® TMS 803, and 1:1 mixture of Wacker-Belsil® PMS MK and Wacker-Belsil® TMS 803, have no measured adhesive force, i.e. same as the reference non-treated surface, whereas the coating with BIO-PSA® 7-4600 (silicone adhesive commercially available from Dow Corning) has a measured adhesive force of about 9 N.

TABLE 3

| Composition | Adhesive Force (N) (mean) |
|---|---|
| Wacker-Belsil ® PMS MK | 0.01 |
| Wacker-Belsil ® TMS 803 | 0.01 |
| Wacker-Belsil ® PMS MK/ Wacker-Belsil ® TMS 803 (1:1 mix) | 0.01 |
| BIO-PSA ® 7-4600 | 9.40 |
| Reference OH-film | 0.01 |

Solubility Tests

The solubility of Wacker-Belsil® PMS MK (T-silicone resin), Wacker-Belsil® TMS 803 (MQ-silicone resin) and SilForm Flexible Resin (MT-silicone resin) in hexamethyldisiloxane (HMDS) was studied. The respective solid resins were added to HMDS solutions and the resulting mixtures were mixed at room temperature using a speed mixer for 2 minutes, and then stored at room temperature overnight. The resulting mixtures were subsequently visually examined and the results are presented in Table 4 below. "Soluble" in Table 4 should be understood to mean a clear and fluid solution with no precipitation

TABLE 4

| Concentration (weight %) | Wacker-Belsil ® TMS 803 | Silform Flexible resin | Wacker-Belsil ® PMS- MK |
|---|---|---|---|
| 10 | soluble | Soluble | soluble |
| 20 | soluble | Soluble | soluble |
| 30 | soluble | Soluble | soluble |
| 40 | soluble | Soluble | soluble |
| 50 | soluble | Soluble | soluble |

The invention claimed is:

1. A method of attaching a medical device to a surface, said medical device having at least one adhesive area comprising an adhesive, wherein said method comprises the steps of:
   contacting said surface with a composition comprising a T silicone resin and/or a DT silicone resin and/or an MQ silicone resin and/or an MT silicone resin, said resin(s) being three-dimensionally crosslinked polysiloxanes having a backbone of silicon and oxygen atoms, drying said composition on said surface, thereby providing a non-tacky coating on said surface; and
   attaching said at least one adhesive area comprising said adhesive to said surface such that said composition is located between, and in contact with, said surface and said adhesive on said at least one adhesive area, thereby attaching said medical device to said surface.

2. The method according to claim 1, wherein
   said T silicone resin comprises T-units having the general formula $RSiO_{3/2}$;
   said DT silicone resin comprises D-units having the general formula $R_2SiO_{2/2}$ and T-units having the general formula $RSiO_{3/2}$; wherein the ratio between the number of R-groups and number of Si atoms in said DT silicone resin is $1.0 < R:Si \leq 1.7$;
   said MQ silicone resin comprises M-units having the general formula $R_3SiO_{1/2}$ and Q-units having the general formula $SiO_{4/2}$; wherein the ratio of the number of M-units and number of Q-units is 0.5-2;
   said MT silicone resin comprises M-units having the general formula $R_3SiO_{1/2}$ and T-units having the general formula $RSiO_{3/2}$; wherein the ratio of the number of M-units and number of T-units is 0.4-1.8;
   wherein the R group is a hydroxyl group and/or a monovalent or functionally substituted C1-C6 hydrocarbon group.

3. The method according to claim 1, wherein said composition comprises an MQ silicone resin wherein at least 80 mol % of the resin molecules thereof are comprised of M-units and Q-units.

4. The method according to claim 1, wherein said composition comprises a DT silicone resin wherein at least 80 mol % of the resin molecules thereof are comprised of D-units and T-units.

5. The method according to claim 1, wherein said composition comprises a T silicone resin wherein at least 80 mol % of the resin molecules thereof are comprised of T-units.

6. The method according to claim 1, wherein said composition comprises an MT silicone resin wherein at least 80 mol % of the resin molecules thereof are comprised of M-units and T-units.

7. The method according to claim 1, wherein said composition further comprising a solvent selected from the group consisting of hexamethyldisiloxane (HMDS), dimethicone, cyclopentasiloxane, C9-C13 isoparafin, isopropyl myristate, ethyl acetate, ethanol, and isopropanol, or a mixture thereof.

8. The method according to claim 7, wherein said composition comprises a mixture of:
   from 1 to 50 weight percent of said T silicone resin and/or said DT silicone resin and/or said MQ silicone resin and/or said MT silicone resin; and
   from 50 to 99 weight percent of said solvent.

9. The method according to claim 1, wherein said T silicone resin and/or said DT silicone resin and/or said MQ silicone resin and/or said MT silicone resin having an average molecular weight in the range of 1000 to 20000 g/mol.

10. The method according to claim 1, wherein said surface is a dermal surface.

11. The method according to claim 1, wherein said medical device is a dressing.

12. The method according to claim 1, wherein said adhesive comprises a soft silicone gel adhesive having a softness of 8 to 22 mm.

13. The method according to claim 1, wherein said step of contacting said surface involves applying said composition in the form of a spray, mousse, aerosol, foam, or by sponge applicator, or by brush, or by stick, or by roller, or by spreading with a spatula, or by release by a release sheet.

14. The method according to claim 1, wherein said step of contacting said surface involves providing a continuous coating or film of said composition on said surface, wherein said coating or film having a coating weight in the range from 0.01 to 30 g/m².

* * * * *